US010021277B2

(12) United States Patent
Oda et al.

(10) Patent No.: US 10,021,277 B2
(45) Date of Patent: Jul. 10, 2018

(54) TERAHERTZ IMAGING DEVICE, AND METHOD OF ELIMINATING INTERFERENCE PATTERNS FROM TERAHERTZ IMAGE

(71) Applicants: NEC Corporation, Tokyo (JP); National Institute of Information and Communications Technology, Tokyo (JP)

(72) Inventors: Naoki Oda, Tokyo (JP); Iwao Hosako, Tokyo (JP); Norihiko Sekine, Tokyo (JP)

(73) Assignees: NEC CORPORATION, Tokyo (JP); NATIONAL INSTITUTE OF INFORMATION AND COMMUNICATIONS TECHNOLOGY, Tokyo (JP)

( * ) Notice: Subject to any disclaimer, the term of this patent is extended or adjusted under 35 U.S.C. 154(b) by 348 days.

(21) Appl. No.: 13/845,569

(22) Filed: Mar. 18, 2013

(65) Prior Publication Data

US 2013/0265415 A1  Oct. 10, 2013

(30) Foreign Application Priority Data

Apr. 4, 2012  (JP) .................. 2012-085471

(51) Int. Cl.
*H04N 5/217* (2011.01)
*G01N 21/3581* (2014.01)
*G01N 21/88* (2006.01)

(52) U.S. Cl.
CPC ......... *H04N 5/217* (2013.01); *G01N 21/3581* (2013.01); *G01N 21/8806* (2013.01); *G01N 21/8851* (2013.01)

(58) Field of Classification Search
CPC .......................................... H04N 5/217
USPC ................................................ 348/131
See application file for complete search history.

(56) References Cited

U.S. PATENT DOCUMENTS

| | | | | |
|---|---|---|---|---|
| 2006/0273255 A1* | 12/2006 | Volkov et al. | ............. | 250/336.1 |
| 2007/0042315 A1* | 2/2007 | Boutoussov et al. | ........... | 433/29 |
| 2007/0115003 A1* | 5/2007 | Nikawa | ........................ | 324/501 |
| 2010/0142800 A1* | 6/2010 | Tung-Sing Pak et al. | ... | 382/149 |

(Continued)

FOREIGN PATENT DOCUMENTS

| | | |
|---|---|---|
| JP | 0518713 A | 1/1993 |
| JP | 2008-249577 A | 10/2008 |
| JP | 2012-13632 A | 1/2012 |

OTHER PUBLICATIONS

Barry N. Behnken, et al., "Optimization of a 3.6-THz Quantum Cascade Laser for Real-Time Imaging with a Microbolometer Focal Plane Array", Processing of SPIE, 2008, pp. 1-9, vol. 68930.

(Continued)

*Primary Examiner* — Jonathan Messmore
(74) *Attorney, Agent, or Firm* — Sughrue Mion, PLLC

(57) ABSTRACT

A sample is irradiated with terahertz light from a light source, so that an image (G1) is generated by capturing an image of a region (R1) including a point (S) of the sample, and an image (G2) is generated by capturing an image of a region (R2) including the point (S) and separated from the region (R1) by a distance (L). A single image (V) is generated by applying a predetermined binary operation to the images (G1) and (G2).

18 Claims, 12 Drawing Sheets

(56) References Cited

U.S. PATENT DOCUMENTS

2010/0171835 A1*  7/2010  Kasai ................... G01N 21/255
                                                    348/162
2013/0044209 A1*  2/2013  Hwang ................ G01N 21/896
                                                    348/128
2013/0076912 A1*  3/2013  Oda et al. ..................... 348/164

OTHER PUBLICATIONS

Alan W. M. Lee, et al., "Real-Time Imaging Using a 4.3-THz Quantum Cascade Laser and a 320 × 240 Microbolometer Focal-Plane Array", IEEE Photonics Technology Letters, Jul. 1, 2006, pp. 1415-1417, vol. 18, No. 13.

Communication dated Feb. 17, 2016 from the Japanese Patent Office in counterpart application No. 2012-085471.

Vinokurov et al., "Speckle pattern of the images of objects exposed to monochromatic coherent terahertz radiation," Quantum Electronics 39 (5) 481-486 (May 2009).

Communication dated May 25, 2016, from the Japanese Patent Office in counterpart Japanese application No. 2012-085471.

* cited by examiner

TERAHERTZ IMAGING DEVICE, AND METHOD OF ELIMINATING INTERFERENCE PATTERNS FROM TERAHERTZ IMAGE

This application is based upon and claims the benefit of priority from Japanese patent application No. 2012-085471, filed on Apr. 4, 2012, the disclosure of which is incorporated herein in its entirety by reference.

BACKGROUND OF THE INVENTION

Field of the Invention

This invention relates to defect detection performed by irradiating samples with terahertz light. The invention in particular relates to elimination of interference patterns caused by terahertz light. The "terahertz light" as used herein is assumed to contain electromagnetic radiation particularly with a frequency range of 100 GHz to 10 THz.

Description of Related Art

Unlike X-rays, terahertz radiation is non-ionizing electromagnetic radiation which is safe to human health, and yet is very transmissive to various materials such as paper, plastics, semiconductors, or the like. Therefore, great expectations are placed on terahertz radiation as effective radiation for detecting defects that cannot be detected with X-rays, visible light, infrared light or the like.

While it is quite difficult to find a terahertz imaging device which is able to acquire images in real time, an imaging device which images a sample using a terahertz light source and a terahertz camera is disclosed, for example, in B. N. Behnken et al., Proc. SPIE Vol. 6893 (2008) p 68930L, FIG. 6 (hereafter, referred to as Non-Patent Document 1), and A. W. M. Lee et al., IEEE PHOTONICS TECHNOLOGY LETTERS, Vol. 18 (2006) p 1415 (hereafter, referred to as Non-Patent Document 2).

Non-Patent Document 1 describes an experimental arrangement as shown in FIG. 9. Referring to FIG. 9, a quantum cascade laser 100 is attached to a cryostat 101 to be cooled to about 10 K and emits 3.6 THz monochromatic waves. The quantum cascade laser has a peak power of about 5 mW and is driven with a duty cycle of about 20%. Thus, the quantum cascade laser has a time-average power of about 1 mW. Monochromatic light from the quantum cascade laser is transformed into collimated beams by a first off-axis paraboloidal minor 102 (F/1, with focal length of 50.8 mm) and applied to a sample 103 placed on a sample plane. The terahertz radiation passing through the sample is focused into an image on an infrared light detecting microbolometer array sensor 106 with 160×120 pixels (frame rate of 30 Hz) mounted on a camera 105, by a second off-axis paraboloidal mirror 104 (F/2, with focal length of 101.6 mm).

A terahertz image 107 obtained by the aforementioned arrangement is shown in FIG. 10. In Non-Patent Document 1, a steel blade covered with two layers of vinyl tape is used as the sample. Whereas Non-Patent Document 1 says that the steel blade is clearly recognized in the image, it can be seen from FIG. 10 that concentric interference patterns 108 have appeared together with the image of the blade. These interference patterns 108 are generated due to high coherency of the quantum cascade laser.

Non-Patent Document 2 describes an experimental arrangement as shown in FIG. 11. A quantum cascade laser 200 is attached to a cryostat 201 to be cooled to about 33 K and emits 4.3 THz monochromatic waves. The quantum cascade laser has a peak power of about 50 mW and is driven by a duty cycle of 25%. Thus, the quantum cascade laser has a time-average power of about 12.5 mW. Monochromatic light from the quantum cascade laser is transformed by a first off-axis paraboloidal minor 202 (F/1, with focal length of 50 mm) into collimated beams, which are collected by a second off-axis paraboloidal mirror 203 (F/2, focal length 100 mm) and applied to an envelope (sample) 204. An image of the envelope is formed on an infrared light detecting microbolometer array sensor 207 with 320×240 pixels in a camera 206 through a silicon lens 205 (F/1, with focal length of 25 mm). A terahertz image 208 obtained by this arrangement is shown in FIG. 12. Characters 209 of "MIT" written on the envelope with a pencil can be recognized clearly.

As seen from FIG. 10, the image obtained by the apparatus described in Non-Patent Document 1 includes not only the steel blade to be detected but also concentric interference patterns 108 generated due to high coherency of the quantum cascade laser. The presence of the interference patterns 108 makes it difficult to view the object to be detected.

Whereas there exist light sources with low coherency, luminance of this type of light source is not so high as that of a quantum cascade laser. For this reason, when the same inspection is conducted using a light source with a low coherency, a high signal-to-noise ratio cannot be obtained, and thus it is difficult to apply the light source to a field of non-destructive inspection of defects in a material or the like.

A backward-wave tube is one of monochromatic light sources with high coherency and high luminance. Interference patterns are generated also in a backward-wave tube. In order to reduce the interference patterns, for example, the tube voltage may be changed at an operating point of 1 kV by about 50 V, but it is impossible to eliminate the interference patterns completely.

It is also conceivable to use a spatial filter in image processing for eliminating such interference patterns. However, when defects of a material are to be detected, the spatial filter may delete the defects. Therefore, a better method is desired.

No interference patterns are recognized in FIG. 12 principally because in the arrangement shown in FIG. 11, the beams are likely focused at a focal position of the second off-axis paraboloidal mirror 203 in order to extract only main beams of the beam patterns from the quantum cascade laser, and the interference patterns are made thinner by diffusion and scattering by the paper envelope as the sample. Even if aperture is set, diffraction patterns due to aperture edge likely appear in a long-wavelength region such as terahertz radiation. Thus, the method described in Non-Patent Document 2 is believed to be greatly affected by diffusion and scattering caused by paper.

As described above, currently available terahertz light sources with high luminance have high coherency. Therefore, when terahertz imaging technology is applied to a field of non-destructive inspection of defects in materials or the like, it will face a problem of presence of interference patterns.

This invention has been made in view of such circumstances, and an object of the invention is that, in inspection performed by irradiating a sample with beams from a terahertz light source and capturing an image of the sample with a terahertz camera, interference patterns caused by terahertz light are eliminated by the image so as to facilitate visual inspection of an object to be inspected.

SUMMARY OF THE INVENTION

As an aspect of the present invention, a terahertz imaging device comprising: a light source for emitting terahertz light;

an imaging element capable of photographing terahertz light for imaging a sample irradiated with the terahertz light from the light source; and an image processing device for generating a single image by applying a predetermined binary operation to a first image and a second image, the first image being generated by irradiating the sample with terahertz light from the light source and capturing an image of a first region including a point of the sample by means of the imaging element, the second image being generated by irradiating the sample with terahertz light from the light source and capturing, by means of the imaging element, an image of a second region including the point and separated from the first region by a predetermined distance is provided.

As another aspect of the present invention, a non-transitory computer-readable medium storing a program for causing a computer to execute the steps of: generating an first image by irradiating a sample with terahertz light from a light source emitting terahertz light and capturing an image of a first region including a point of the sample by means of an imaging element capable of photographing terahertz light; generating an second image by irradiating the sample with terahertz light from the light source and capturing, by means of the imaging element, an image of a second region including the point and separated from the first region by a predetermined distance; and generating a single image by applying a predetermined binary operation to the first and second images is provided.

As another aspect of the present invention, a method of eliminating an interference pattern from a terahertz image comprising the steps of: generating an first image by irradiating a sample with terahertz light from a light source emitting terahertz light and capturing an image of a first region including a point of the sample by means of an imaging element capable of photographing terahertz light; generating a second image by irradiating the sample with terahertz light from the light source and capturing, by means of the imaging element, an image of a second region including the point and separated from the first region by a predetermined distance; and generating a single image by applying a predetermined binary operation to the first and second images is provided.

DETAILED DESCRIPTION OF THE PREFERRED EMBODIMENTS

Figure 1:
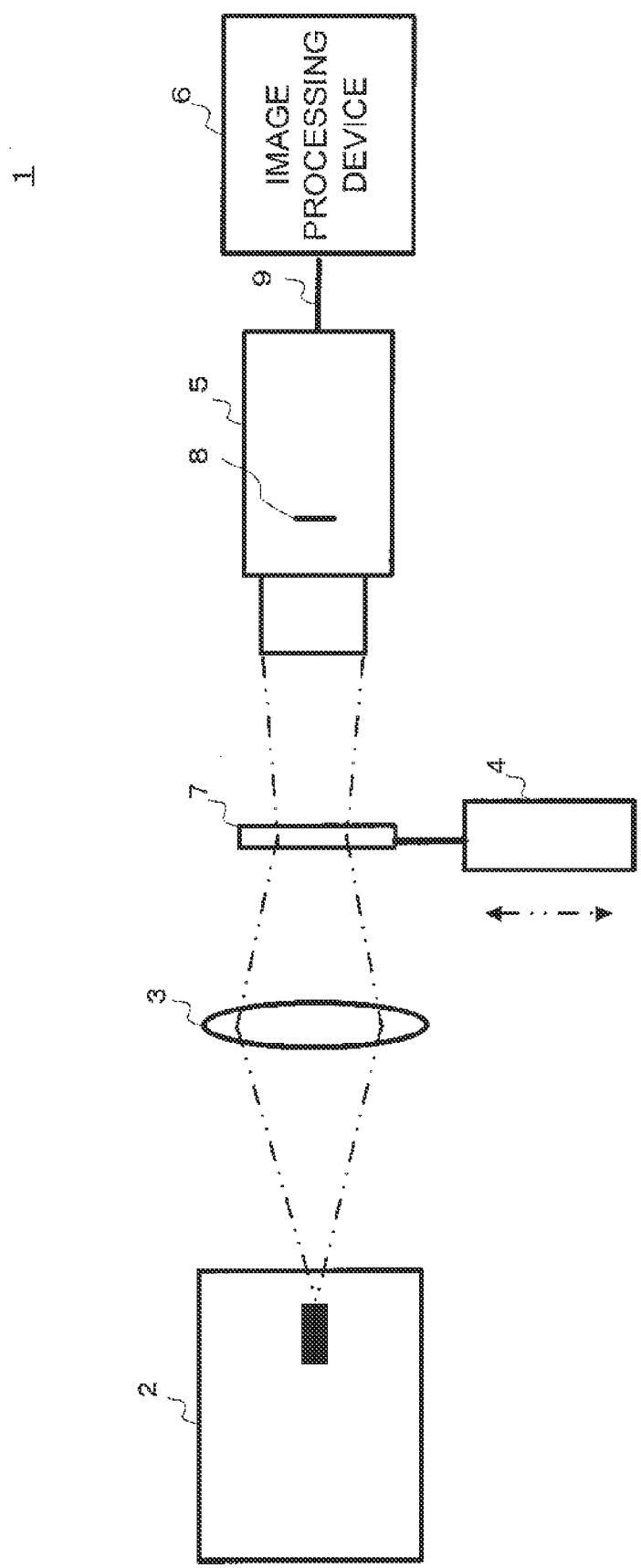
FIG. 1 is a block diagram showing an imaging device for defect detection 1 according an embodiment of the invention.

An imaging device for defect detection 1 according to an embodiment of the invention will be described with reference to FIG. 1. The imaging device for defect detection 1 has a terahertz light source 2, an optical system 3, a stage 4, a terahertz camera 5, and an image processing device 6.

The terahertz light source 2 may be provided, for example, by a quantum cascade laser, a backward-wave tube, a high-luminance terahertz light source such as a resonance tunneling array, a frequency-tunable terahertz parametric oscillator, or the like.

The optical system 3 collimates or transforms a divergent beam emitted by the terahertz light source 2 into a convergent beam, and guides it to a sample 7 placed on the stage 4.

The stage 4 moves the sample 7 placed thereon in a plane that is substantially perpendicular to an optical axis, as indicated by the arrows in FIG. 1. The stage 4 may be either a uniaxial stage or a biaxial stage.

The terahertz camera 5 is a camera for generating an image by capturing an image of the sample 7 irradiated with terahertz radiation. The terahertz camera has, as the imaging element 8, a two-dimensional bolometer array sensor which has sensitivity to terahertz radiation, and outputs an image signal 9.

The image processing device 6 is a signal processing device for processing the image signal 9.

Next, operation of the imaging device for defect detection 1 will be described. One of objects of the invention is to detect defects in a material that is intended to be produced homogeneously. The inventors of this invention have found that defects in such a material are generally so small that even if the material is moved, interference patterns caused by a high-luminance high-coherency terahertz light source do not change significantly.

Figure 2:
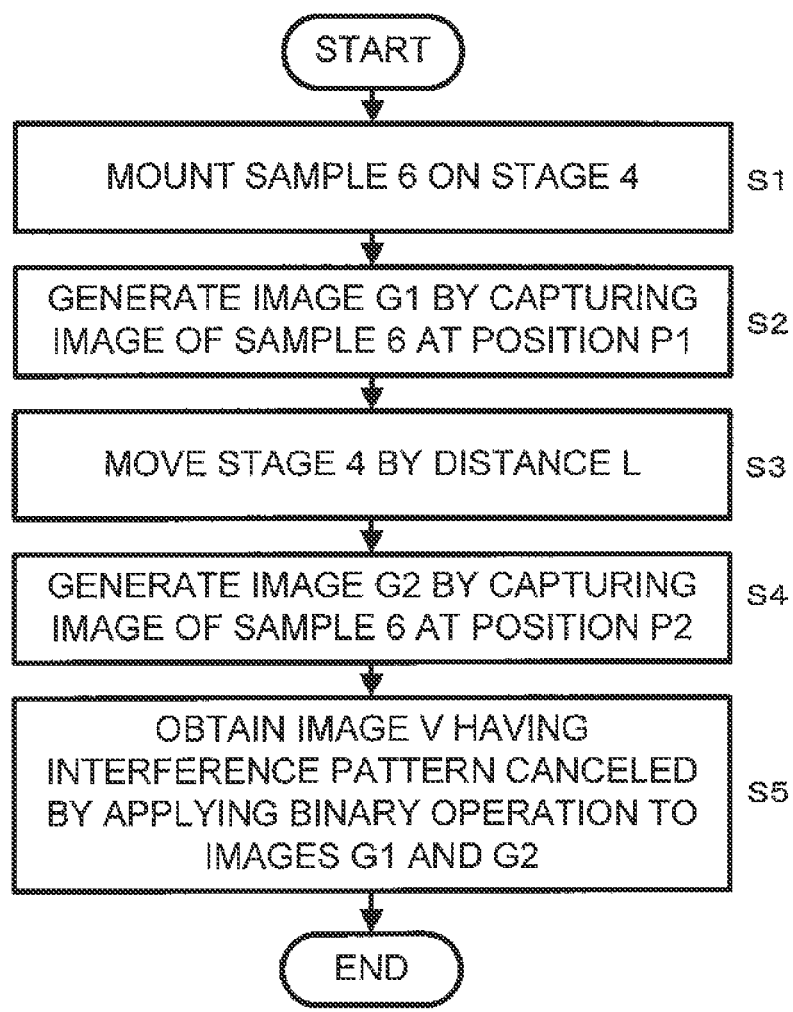
FIG. 2 is a flowchart for explaining a method of generating an image from which interference patterns have been eliminated by the imaging device 1.

According to the invention based on this finding, images are generated before and after moving the material, that is, the sample 7, and an image is generated by canceling out interference patterns from these images. Referring to FIG. 2, a sample 7 is placed on the stage 4 (step S1), and an image of the sample 7 is captured at a position P1 to generate an image G1 containing an object to be detected X such as a defect of the sample 7 (step S2). The sample 7 is then moved from the position P1 to a position P2 by a distance L (step S3), and an image of the sample is captured at the position 2 to generate an image G2 containing the object to be detected X (step S4). Finally, an image V is generated by the image processing device 6 performing a binary operation on the images G1 and G2, more specifically, obtaining a difference or ratio between the images G1 and G2 (step S5).

An object to be detected X must be contained in both of the images G1 and G2. Therefore, an imaged region of the sample 7 in the image G1 and an imaged region of the sample 7 in the image G2 must overlap at least partially. Specifically, when the image G1 is generated by imaging a region R1 containing a point S of the sample 7, the image G2 must be generated by imaging a region R2 which contains the point S but is different from the region R1. A distance between the position P1 and the position P2 corresponds to such a distance that the images G1 and G2 can be imaged. This distance is determined according to a field of view of the terahertz camera 5, and a positional relationship between the light receiving surface of the imaging element 8 and the sample 7.

As described above, the image G1 and the image G2 have substantially the same interference patterns, and hence the interference patterns in the images G1 and G2 are canceled with each other by obtaining a difference or ratio between them. As a result, the interference patterns can be eliminated from the image V.

On the other hand, actually a single object to be detected X appears as two images X1 and X2 in the image V. The images X1 and X2 appear in the image V at positions separated by a distance M. The distance M is determined according to a moving distance L of the sample 7, and a scale reduction ratio R defined by a positional relationship between the sample 7 and a lens of the terahertz camera 5. For example, when the distance L is 1.5 mm, and the scale reduction ratio R of the sample is ½, the images X1 and X2 appear in the image V at positions separated by the distance M=LR=0.75 mm.

The images X1 and X2 are in different forms depending on a type of the binary operation. When the image V is generated as a difference between the image G1 and the image G2, one of the images X1 and X2 appears as a positive signal while the other image appears as a negative signal. When the image V is generated as a ratio between the image G1 and the image G2, one of the images X1 and X2 appears as a signal with a value of one or more, while the other image appears as a signal with a value of one or less.

In the method of FIG. 2, as described above, the interference patterns are eliminated by generating the image V from the image G1 at the position P1 and the image G2 at the position P2. Although in the description above, each of the images G1, G2, V is generated once, the signal-to-noise ratio can be improved by generating these images for a plurality of times, integrating these images, and obtaining an average of the image V.

Figure 3:
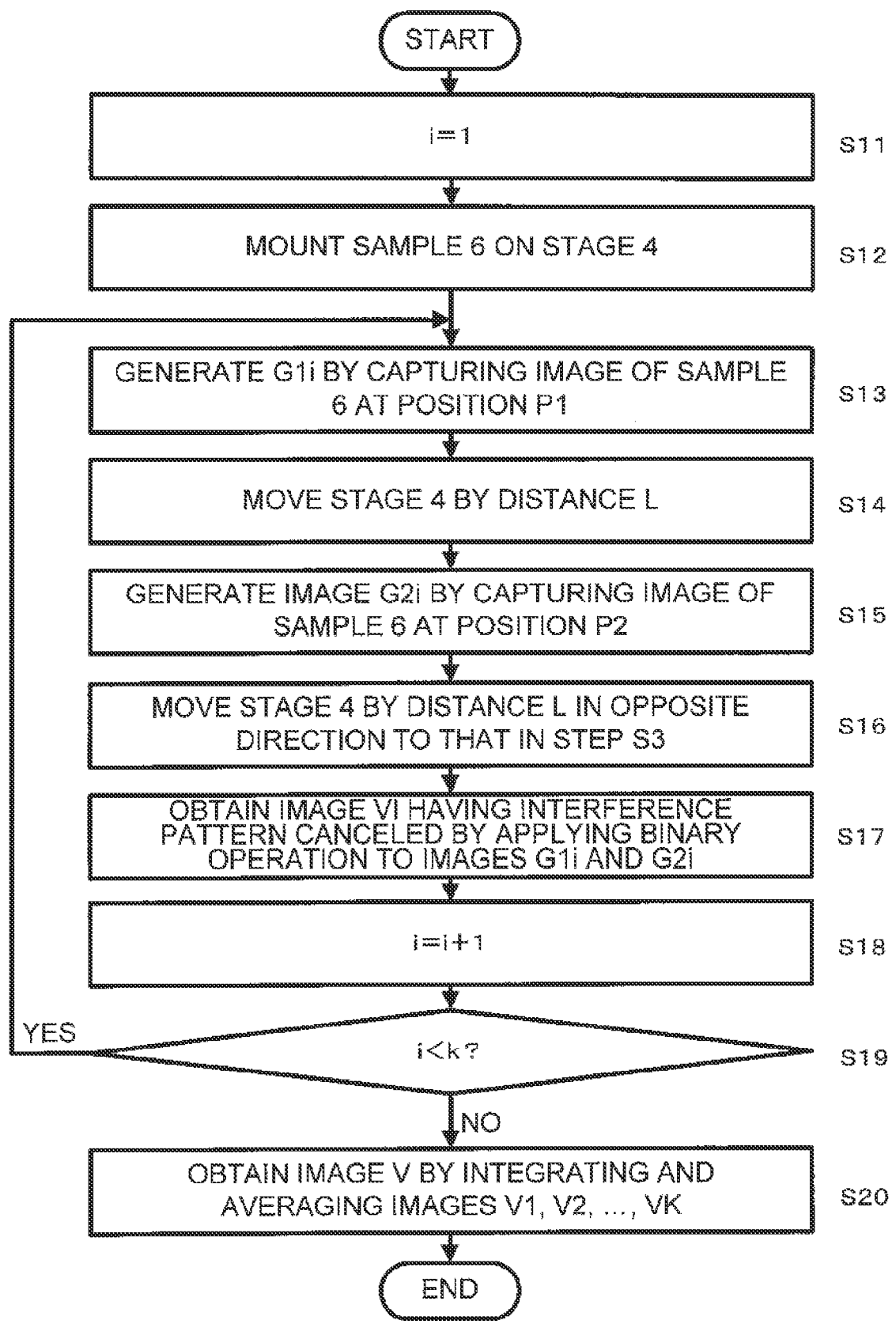
FIG. 3 is a flowchart for explaining another method of generating an image from which interference patterns have been eliminated by the imaging device 1.

Specifically, as shown in FIG. 3, the images G1 and G2 are generated for a plurality of times (k times in this example, k being a natural number of 2 or more) to obtain sets of images (G11, G21), (G12, G22), ..., (G1k, G2k). Images V1, V2, ..., Vk are obtained respectively from these sets of images (steps S11 to S19), and the images V1, V2, ..., Vk are integrated to obtain an average so that the image V is obtained (step S20). In this manner, the signal-to-noise ratio can be further improved.

Exemplary Embodiment 1

Referring to FIG. 1, Exemplary embodiment 1 of the invention will be described. In Exemplary embodiment 1, a quantum cascade laser is used as the terahertz light source 2. The quantum cascade laser is cooled with liquid nitrogen, having an oscillation frequency of 3.7 THz, and a time-average power of 5 µW. The sample 7 is irradiated in a region with a diameter of about 11 mm. The terahertz camera 5 has an F value of 0.8 and a focal length of 28 mm. A microbolometer array sensor with 320×240 pixels is used as the imaging element 8 of the terahertz camera 5. The distance between the lens of the terahertz camera 5 and the sample 7 is 84 mm. The reduction ratio is 2:1 according to the positional relationship between the sample 7 and the lens of the terahertz camera 5. The stage 4 is a biaxial stage.

Figure 4A:
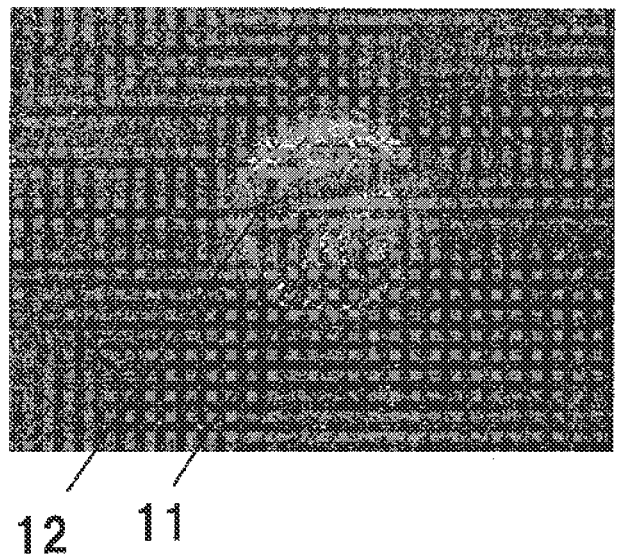
FIGS. 4A and 4B show terahertz images generated by capturing an image of a sample 7, FIG. 4A showing an image G1 generated when a stage 4 is at a position P1, FIG. 4B showing an image G2 generated when the stage 4 is at a position P2 that is lower than the position P1 by a distance L of 1.5 mm.
Figure 4B:
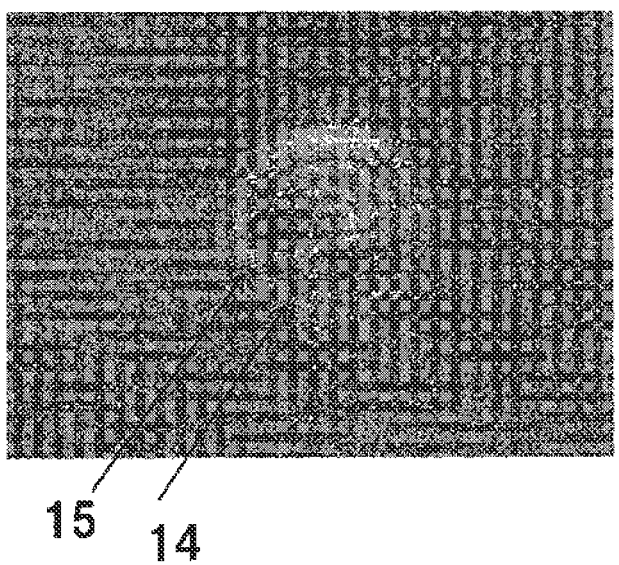

This system is operated as described in the flowchart of FIG. 2. A divergent beam emitted by the terahertz light source 2 is collimated or transformed into a convergent beam by the optical system 3, and applied to the sample 7. In step S2, a terahertz image G1 is generated by imaging the sample 7 when the stage 4 is at the position P1, and this terahertz image G1 is shown in FIG. 4A. In step S3, the stage 4 is moved by a distance L of 1.5 mm from the position P1 to the position P2 located below the position P1. In step S4, a terahertz image G2 is generated by imaging the sample 7, and this terahertz image G2 is shown in FIG. 4B.

In FIG. 4A, an image 10 that is the terahertz image G1 shows a concentric interference pattern 11 at the position P1 and a defect shape 12 present in the sample 7. In FIG. 4B, an image 13 that is the terahertz image G2 shows a concentric interference pattern 14 at the position P2 and a defect shape 15 present in the sample 7. Attention should be paid to the fact that whereas the defect shapes 12 and 15 appear at different positions in the images 10 and 13, these defect shapes are actually the same defect shape. The positions where these defects shapes appear deviate from each other, for the reason that the stage 4 has been moved downward from the position P1 to the position P2 as described above.

Figure 5A:
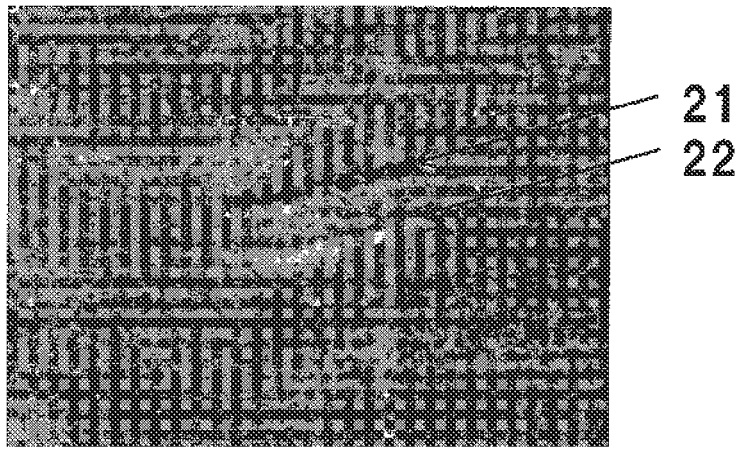
FIGS. 5A and 5B show images V generated by applying binary operation on the images G1 and G, FIG. 5A showing an image 20 generated by obtaining a difference between the image 10 and the image 13, FIG. 5B showing an image 23 generated by dividing the image G1 by the image G2.
Figure 5B:
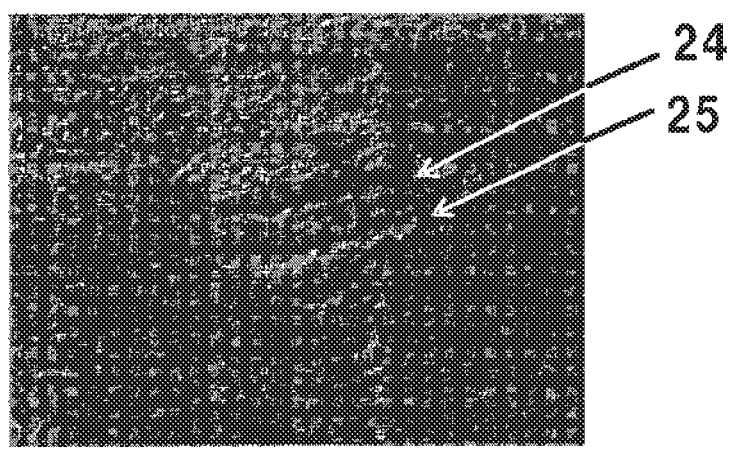

In step S5, an image V is generated by performing a binary operation on the images 10 and 13, and this image V is shown in FIGS. 5A and 5B. FIG. 5A shows an image 20 that is generated by obtaining a difference between the image 10 and the image 13. As seen from FIG. 5A, the interference pattern in the images 10 and 13 has been eliminated, and defect shapes 21 and 22 have appeared. Since the interference patterns 11 and 14 appear at almost the same positions in the images 10 and 13, the interference patterns 11 and 14 are canceled with each other, whereby they are eliminated from the image 20.

The defect shape 21 corresponds to the defect shape 12, and the defect shape 22 corresponds to the defect shape 15. The defect shape 21 appears as a negative signal, while the defect shape 22 appears as a positive signal. As said before, the defect shapes 21 and 22 are actually the same defect shape. While in this exemplary embodiment, a microbolometer array sensor with 320×240 pixels is used as the imaging element 8, the distance between the defect shapes 21 and 22 was 0.75 mm. This distance is attributed to the moving distance L of the stage 4 being 1.5 mm and the reduction of 2:1, and a relationship of 1.5 mm/2=0.75 mm is established. When a difference between the images is obtained by the binary operation, defect shapes which are actually the same appear, on the image V, as a signal pair consisting of a positive and negative signal separated by a distance defined according to the moving distance of the stage 4 and the scale reduction.

An image 23 generated by dividing the image 10 by the image 11 in the binary operation in step S5 is shown in FIG. 5B. Like the image 20 of FIG. 5A, the concentric interference pattern has been eliminated and the defect shapes 24 can 25 be viewed clearly. This is because, as described in relation to FIG. 5A, since the positions where the interference patterns 11 and 14 appear are about the same between the images 10 and 13, these interference patterns are canceled with each other and eliminated from the image 23 by obtaining a quotient between the images 10 and 13.

The defect shape 24 corresponds to the defect shape 12, and the defect shape 25 corresponds to the defect shape 15. While the defect shape 24 appears as a signal with a value of 1 or less, the defect shape 25 appears as a signal with a value of 1 or more. As described in the above, the defect shapes 24 and 25 are actually the same defect shape, and the distance between these defect shapes is also 0.75 mm. When a quotient is obtained between these images by the binary operation, the result is in agreement on the point that actually the same defect shapes appear on the image V, at positions separated by a distance defined according to a moving distance of the stage 4 and a reduction ratio. Whereas in the image 20 in which a difference is obtained, one defect shape appears as a signal pair consisting of positive and negative signals, in the image 23 in which a quotient is obtained, one defect shape appear as a signal pair consisting of a signal with a value of 1 or more and a signal with a value of 1 or less.

Exemplary Embodiment 2

Figure 6:
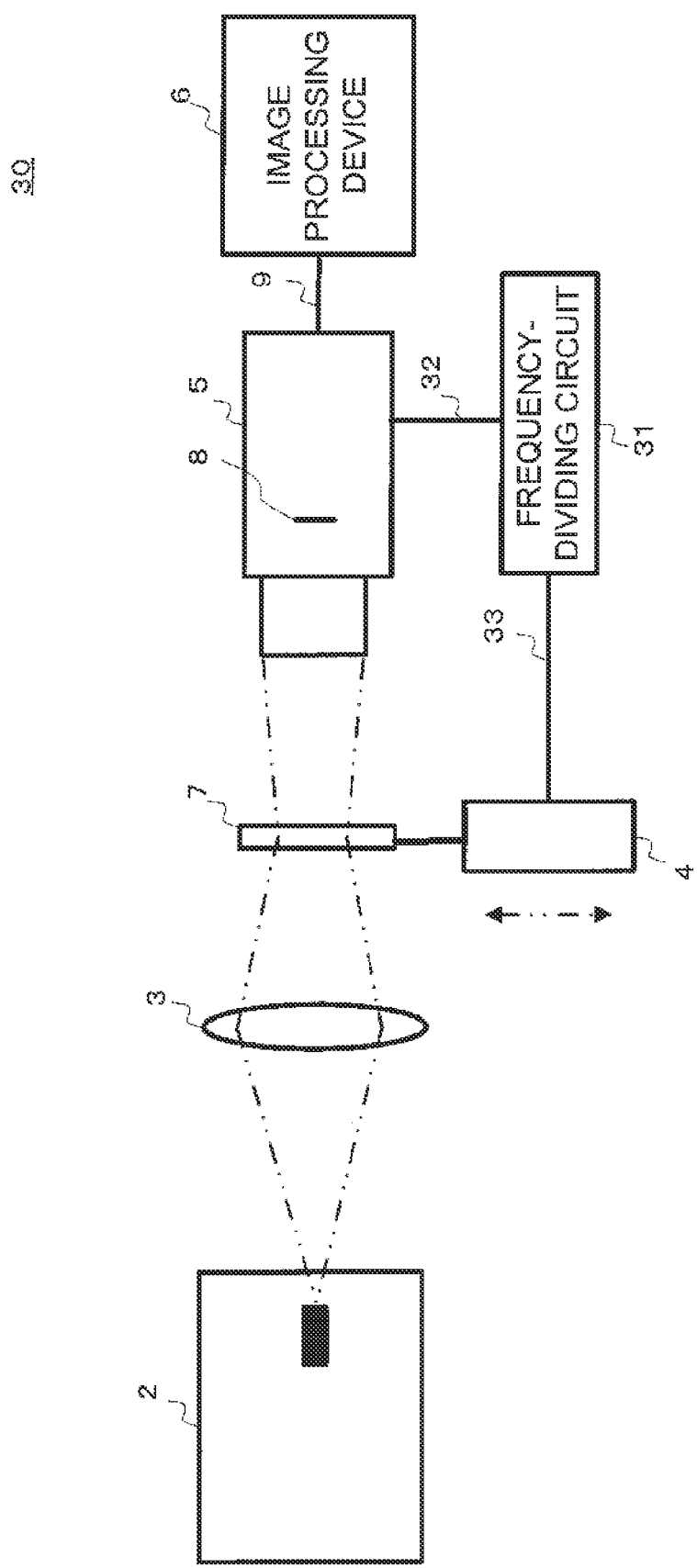
FIG. 6 is a block diagram showing an imaging device for defect detection 30.

Referring to FIG. 6, an imaging device for defect detection 30 will be described. Comparing with the imaging device 1 of FIG. 1, the imaging device 30 is different from the imaging device 1 in having a frequency-dividing circuit 31.

A terahertz camera 5 outputs a synchronizing signal 32 for notifying other devices of an imaging timing of the camera. The synchronizing signal 32 is a rectangular wave synchronized with an imaging frame of the terahertz camera 5, and a rise of the synchronizing signal 32, for example, indicates an imaging timing of the terahertz camera 5.

The frequency-dividing circuit 31 receives the synchronizing signal 32 from the terahertz camera 5, and frequency-divides the synchronizing signal 32 to generate a moving stage control signal 33 which is output to the stage 4. When the synchronizing signal 32 has a frequency indicated by f, the frequency of the moving stage control signal 33 is possibly set to $f/2^n$ (n is an integer).

In response to a rise or fall of a rectangular wave as the moving stage control signal 33, the stage 4 moves between the position P1 and the position P2. For example, when the moving stage control signal 33 varies from high level to low level, the stage 4 accordingly moves to the position P1. In contrast, when the moving stage control signal 33 varies from low level to high level, the stage 4 accordingly moves to the position P2. The correspondence relation between high/low level and position P1/P2 can be opposite.

In this manner, the imaging timing of the terahertz camera 5 is coordinated with the moving timing of the stage 4, so that the imaging device 30 repeatedly performs cycles of operation, each consisting of imaging the sample 7 when the stage 4 is at the position P1 to generate the image G1, and imaging the sample 7 when the stage 4 is at the position P2 to generate the image G2. A plurality of pairs of images G1 and G2 (G11, G21), (G12, G22), (G13, G23), . . . are generated, and images V1, V2, V3, . . . are generated as difference or ratio between the respective pairs of the images. Finally, these images are integrated and averaged to generate the image V.

The invention can also be designed such that the imaging device 30 images the sample for a plurality of times, respectively, when the stage 4 is at the position P1 and when at the position P2 within one cycle. For example, the imaging device 30 can be designed to image twice when the stage 4 is at the position P1 in a certain cycle, and then image twice after the stage 4 is moved to the position P2, so that the imaging device 30 images the sample twice at each of the positions P1 and P2, that is, four times in total within one cycle.

Figure 7:
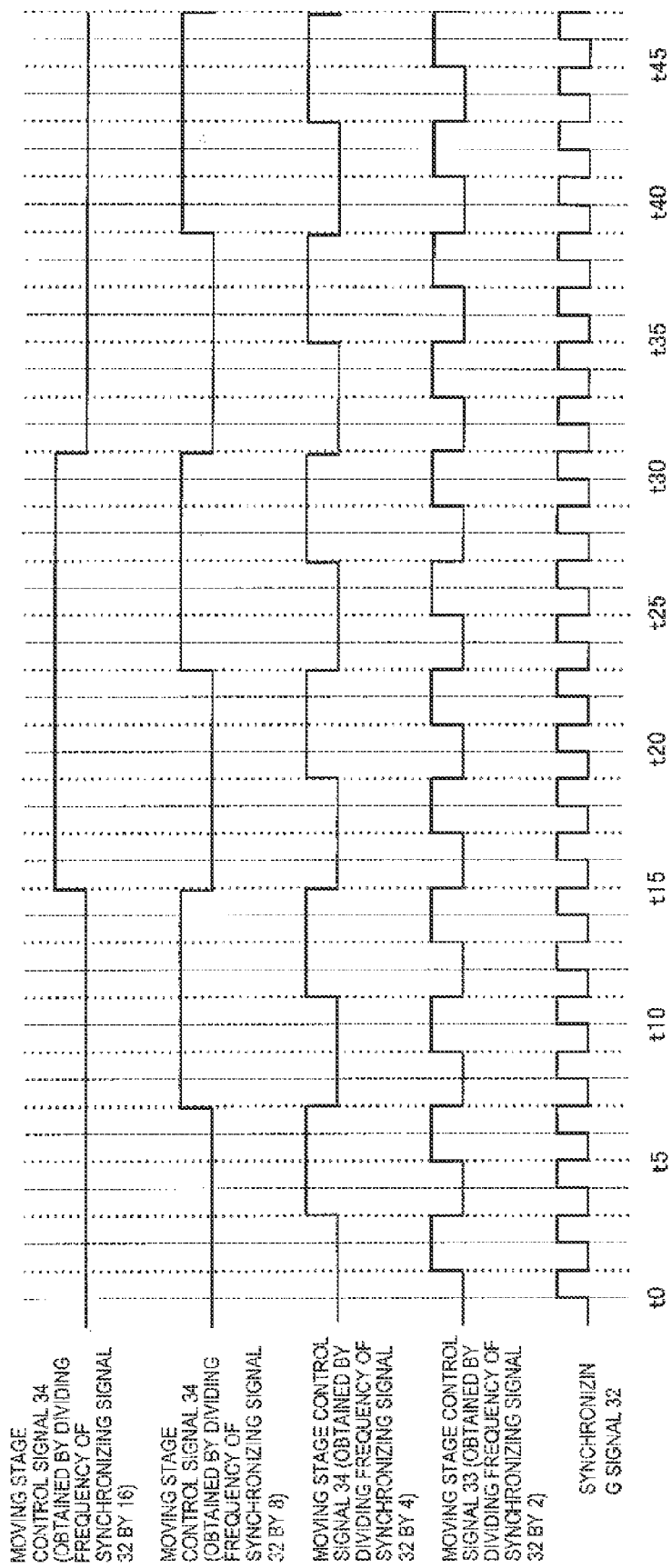
FIG. 7 is a diagram for explaining a relationship between synchronizing signal 32 and moving stage control signal 33.

FIG. 7 shows examples of the moving stage control signal 33 generated by the frequency-dividing circuit 31 dividing the frequency of the synchronizing signal 32 by 2, 4, 8, and 16. The synchronizing signal 32 rises at timings indicated by t with suffixes of even numbers such as $t_0$, $t_2$, $t_4$, . . . (the timings indicated by the chain lines), and the terahertz camera 5 performs imaging at these timings. It is assumed that when the moving stage control signal 33 is at low level, the stage 4 is at the position P1, whereas when the moving stage control signal 33 is at high level, the stage 4 is at the position P2. It can be seen from FIG. 7 that when the stage 4 is controlled with a moving stage control signal 33 that is obtained by dividing the frequency of the synchronizing signal 32 by 2, the terahertz camera 5 captures an image once at each of the positions P1 and P2. Likewise, It can be seen from FIG. 7 that when the stage 4 is controlled with moving stage control signals 33 obtained by dividing the frequency of the synchronizing signal 32 by 4, 8, and 16, the terahertz camera 5 performs imaging twice, four times, and eight times, respectively, at each of the positions P1 and P2. When the synchronizing signal 32 is a 30 Hz rectangular wave synchronized with imaging frames of the terahertz camera 5, and the moving stage control signal 33 is one obtained by dividing the frequency of the synchronizing signal 32 by 16, the moving stage control signal 33 is a rectangular wave with a frequency of 1.875 Hz.

Processes to generate an image V by performing binary operation on a pair of terahertz images G1 and G2 are the same as in Exemplary embodiment 1, and therefore description thereof will be omitted.

Exemplary Embodiment 3

In Exemplary embodiments 1 and 2, an image V from which interference pattern is eliminated are generated by obtaining a difference or ratio between a pair of terahertz images G1 and G2. As described above, when the image V is sharpened, actually the same two defect shapes appear as two images in the image V, and these two images have a predetermined positional relationship that is determined according to the moving distance of the stage and the reduction ratio. This Exemplary embodiment utilizes this to specify two images corresponding to the same defect shape from the image V.

Figure 8:
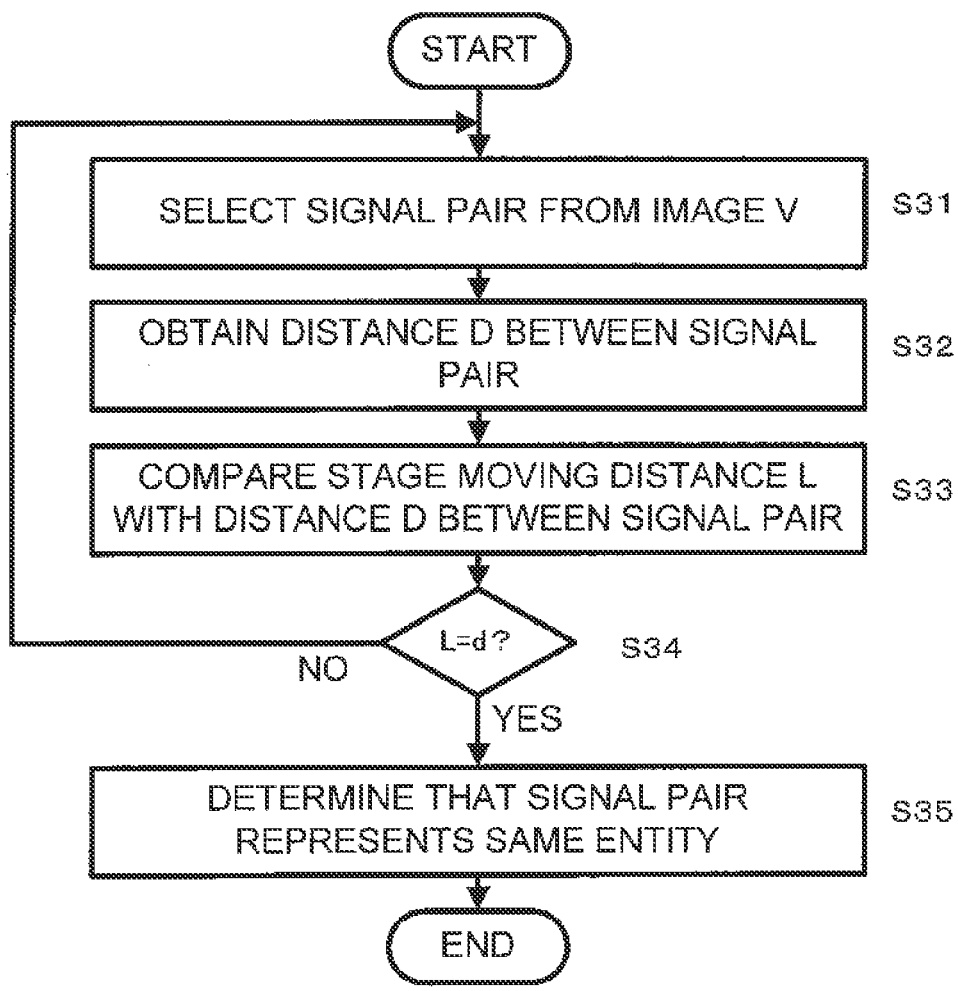
FIG. 8 is a flowchart for explaining a method of determining a signal pair of an image V corresponding to the same entity in the sample 7.
Figure 9:
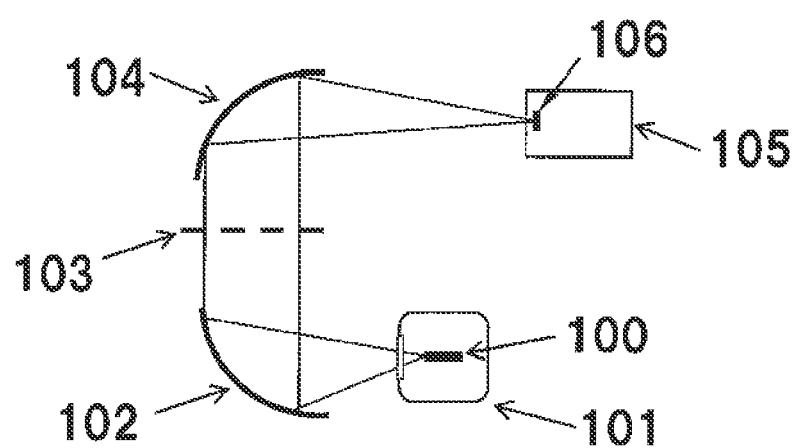
FIG. 9 is a diagram for explaining the experiment described in Non-Patent Document 1.
Figure 10:
FIG. 10 is an image obtained by the experiment described in Non-Patent Document 1.
Figure 11:
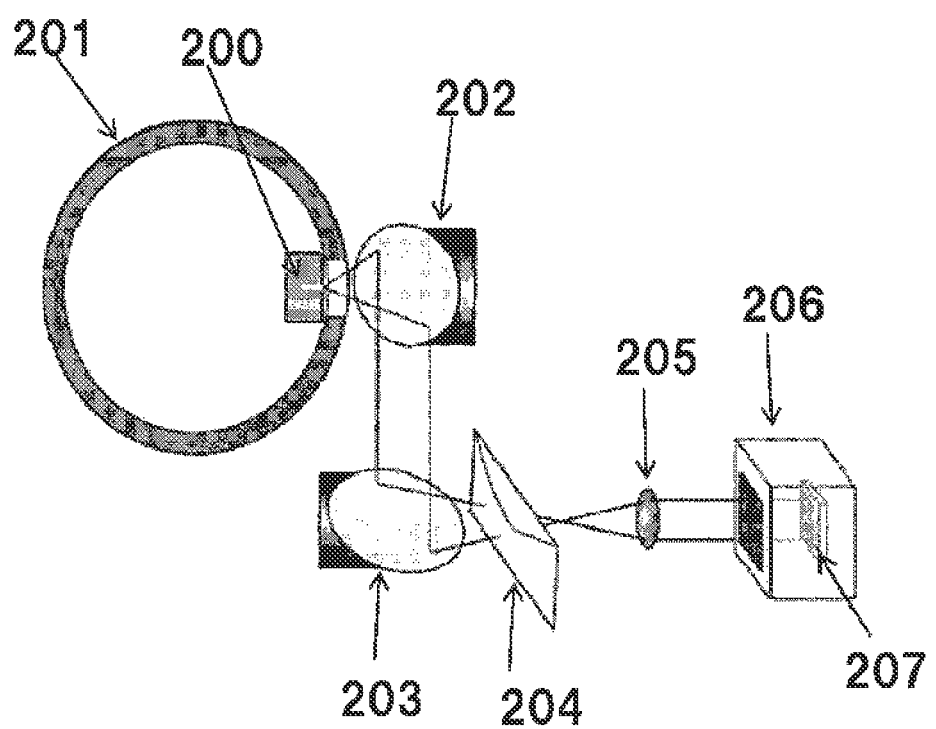
FIG. 11 is a diagram for explaining the experiment described in Non-Patent Document 2.
Figure 12:
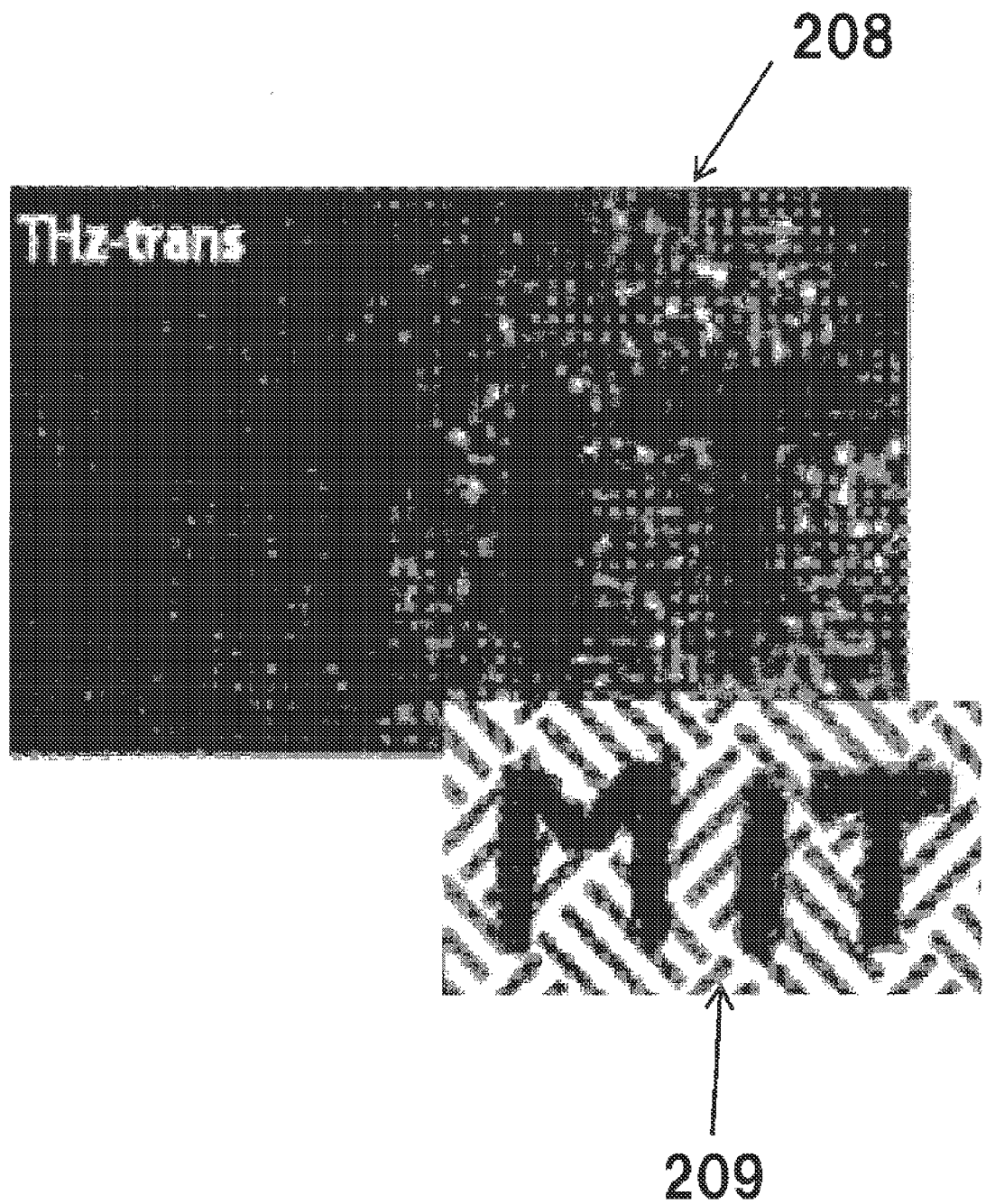
FIG. 12 is an image obtained by the experiment described in Non-Patent Document 2.

This Exemplary embodiment 3 will be described, using the imaging device for defect detection 30 shown in FIG. 6. The imaging device 30 according to this Exemplary embodiment operates as shown in the flowchart of FIG. 8 in continuation from step S20 of FIG. 3.

The image processing device 6 selects a pair of signals corresponding to each other from the image V (step S31). When a difference between the terahertz images G1 and G2 in a binary operation for generating the image V (step S17), one of the signal pair is a positive signal while the other is a negative signal. When a quotient of the terahertz images G1 and G2 is obtained in step S17, one of the signal pair is a signal with a value of 1 or more, while the other is a signal with a value of 1 or less.

Next, a distance between the selected signal pair is obtained (step S32). It is assumed that the pixel pitch of imaging elements 8 such as microbolometer array sensors of the terahertz camera 5 is preliminarily known. A distance between the signal pair can be obtained by counting the number of pixels between the signal pair and multiplying the counted number of pixels by a known pixel pitch.

Next, the distance L in step S14 for which the stage 4 has been moved is compared with the distance obtained in step S32 (steps S33 and S34). When these distances match, the image processing device 6 determined that the signal pair indicates actually the same defect (step S35). If the distances do not match, the processing is repeated after selecting another signal pair in the image V.

According to this Exemplary embodiment 3, a correspondence relationship between two images appearing in the image V and indicating the same entity can be known, and presence of any defect in the material can be detected automatically and non-destructively.

While the invention has been described based on the embodiments and exemplary embodiments, the invention is not limited to these. For example in the imaging device for defect detection 1, images are generated by moving the sample 7 with the stage 4 while the terahertz light source 2, the optical system 3, and the terahertz camera 5 are fixed. However, what is necessary to generate the images G1 and G2 is that the imaging position of the sample 7 by the terahertz camera 5 is moved relatively, and thus it is not always necessary to move the sample with the camera being fixed. Adversely, the images G1 and G2 may be generated by moving the terahertz light source 2, the optical system 3, and the terahertz camera 5 with the sample 7 being fixed.

What is claimed is:

1. A terahertz imaging device comprising:
a light source for emitting terahertz light having a predetermined frequency;
an optical system for transforming the terahertz light into collimated light or a convergent beam;
an imaging element capable of photographing the transformed terahertz light for imaging a sample irradiated with the transformed terahertz light from the optical system, the sample being an object of imaging; and
an image processing device for generating a single image by applying a binary operation to a first image and a second image, the first image being generated by irradiating the sample with the transformed terahertz light from the optical system and capturing an image of a first region including a point of the sample by the imaging element, the second image being generated by irradiating the sample with the transformed terahertz light from the optical system and capturing, by the imaging element, an image of a second region including the point and separated from the first region by a predetermined distance,
wherein
the first image and the second image each includes an interference pattern, and
the image processing device cancels the interference pattern of the first image and the interference pattern of the second image with each other to generate the single image.

2. The terahertz imaging device according to claim 1, further comprising a stage for mounting the sample thereon and moving the sample by the predetermined distance.

3. The terahertz imaging device according to claim 1, wherein generation of the first and second images is performed for a plurality of times for each of the first and second images, and the single image is generated based on the plurality of the first and second images.

4. The terahertz imaging device according to claim 1, wherein the binary operation is an operation to calculate a difference between the first image and the second image.

5. The terahertz imaging device according to claim 1, wherein the binary operation is an operation to calculate a quotient between the first image and the second image.

6. The terahertz imaging device according to claim 1, further comprising a processor for determining whether or not entities in the sample corresponding to a signal pair in the single image are the same based on a result of comparing the predetermined distance with a distance between the signal pair.

7. A non-transitory computer-readable medium storing a program for causing a computer to execute the steps of:
generating a first image by irradiating a sample, which is an object of imaging, with terahertz light having a predetermined frequency from a light source emitting the terahertz light, transforming the terahertz light into collimated light or a convergent beam using an optical system, and capturing an image of a first region including a point of the sample by an imaging element capable of photographing the transformed terahertz light;
generating a second image by irradiating the sample with the transformed terahertz light from the optical system and capturing, by the imaging element, an image of a second region including the point and separated from the first region by a predetermined distance; and
generating a single image by applying a binary operation to the first and second images, wherein the first image and the second image each includes an interference pattern, and
cancelling the interference pattern of the first image and the interference pattern of the second image with each other to generate the single image.

8. The non-transitory computer-readable medium storing a program according to claim 7, wherein the non-transitory computer-readable medium causes the computer to further execute the step of moving a stage on which the sample is mounted by the predetermined distance.

9. The non-transitory computer-readable medium storing a program according to claim 7, wherein the generating of the first and second images is performed for a plurality of times for each of the first and second images, and the single image is generated based on the plurality of first and second images.

10. The non-transitory computer-readable medium storing a program according to claim 7, wherein the binary operation is an operation to calculate a difference between the first image and the second image.

11. The non-transitory computer-readable medium storing a program according to claim 7, wherein the binary operation is an operation to calculate a quotient between the first image and the second image.

12. The non-transitory computer-readable medium storing a program according to claim 7, wherein the non-transitory computer-readable medium causes the computer to further execute the step of determining whether or not entities in the sample corresponding to a signal pair in the single image are the same based on a result of comparing the predetermined distance with a distance between the signal pair.

13. A method of eliminating an interference pattern from a terahertz image, the method comprising the steps of:
transforming terahertz light emitted from a light source and having a predetermined frequency into collimated light or a convergent beam using an optical system;

generating a first image by irradiating a sample, which is an object of imaging, with the transformed terahertz light from the optical system and capturing an image of a first region including a point of the sample by an imaging element capable of photographing the transformed terahertz light;

generating a second image by irradiating the sample with the transformed terahertz light from the optical system and capturing, by the imaging element, an image of a second region including the point and separated from the first region by a predetermined distance; and generating a single image by applying a binary operation to the first and second images, wherein the first image and the second image each includes an interference pattern, and cancelling the interference pattern of the first image and the interference pattern of the second image with each other to generate the single image.

14. The method of eliminating an interference pattern from a terahertz image according to claim 13, further comprising the step of moving a stage on which the sample is mounted by the predetermined distance.

15. The method of eliminating an interference pattern from a terahertz image according to claim 13, wherein the generating of the first and second images is performed for a plurality of times for each of the first and second images, and the single image is generated based on the plurality of first and second images.

16. The method of eliminating an interference pattern from a terahertz image according to claim 13, wherein the binary operation is an operation to calculate a difference between the first image and the second image.

17. The method of eliminating an interference pattern from a terahertz image according to claim 13, wherein the binary operation is an operation to calculate a quotient between the first image and the second image.

18. The method of eliminating an interference pattern from a terahertz image according to claim 13, further comprising the step of determining whether or not entities in the sample corresponding to a signal pair in the single image are the same based on a result of comparing the predetermined distance with a distance between the signal pair.

* * * * *

UNITED STATES PATENT AND TRADEMARK OFFICE
CERTIFICATE OF CORRECTION

PATENT NO. : 10,021,277 B2
APPLICATION NO. : 13/845569
DATED : July 10, 2018
INVENTOR(S) : Naoki Oda et al.

It is certified that error appears in the above-identified patent and that said Letters Patent is hereby corrected as shown below:

In the Specification

Column 1, Background of the Invention, Line 46:
Delete "minor" and insert --mirror-- therefor Column 2, Background of the Invention, Line 4:
Delete "minor" and insert --mirror-- therefor Signed and Sealed this
Twenty-sixth Day of February, 2019

Andrei Iancu
*Director of the United States Patent and Trademark Office*